(12) United States Patent  
Choi et al.

(10) Patent No.: US 9,150,576 B2  
(45) Date of Patent: Oct. 6, 2015

(54) R-7-(3-AMINOMETHYL-4-METHOXYIMINO-3-METHYL-PYRROLIDIN-1-YL)-1-CYCLOPROPYL-6-FLUORO-4-OXO-1 ACID AND L-ASPARTIC ACID SALT, PROCESS FOR THE PREPARATION THEREOF AND PHARMACEUTICAL COMPOSITION COMPRISING THE SAME FOR ANTIMICROBIAL

(71) Applicant: ARIMED, INC., Seoul (KR)

(72) Inventors: Dong Rack Choi, Yongin-si (KR); Jin Yang, Yongin-si (KR); Sue Hye Yoon, Suwon-si (KR); Sung Jae Pyun, Seoul (KR); Seung Hwan Kim, Suwon-si (KR); Seung Kyoo Seong, Incheon (KR); Jei Man Ryu, Anyang-si (KR)

(73) Assignee: ARIMED, INC., Seoul (KR)

( * ) Notice: Subject to any disclaimer, the term of this patent is extended or adjusted under 35 U.S.C. 154(b) by 0 days.

(21) Appl. No.: 14/574,935

(22) Filed: Dec. 18, 2014

(65) Prior Publication Data  
US 2015/0105558 A1 Apr. 16, 2015

Related U.S. Application Data

(63) Continuation of application No. 14/155,249, filed on Jan. 14, 2014, now Pat. No. 8,952,164, which is a continuation of application No. 13/387,080, filed as application No. PCT/KR2010/004938 on Jul. 27, 2010, now Pat. No. 8,664,240.

(30) Foreign Application Priority Data

Jul. 27, 2009 (KR) .................. 10-2009-0068396

(51) Int. Cl.
| | | |
|---|---|---|
| *C07D 471/04* | (2006.01) | |
| *A61K 9/00* | (2006.01) | |
| *A61K 9/14* | (2006.01) | |
| *A61K 9/20* | (2006.01) | |
| *A61K 9/48* | (2006.01) | |
| *A61K 31/4375* | (2006.01) | |
| *C07D 487/04* | (2006.01) | |
| *C07C 229/24* | (2006.01) | |

(52) U.S. Cl.
CPC ............ *C07D 471/04* (2013.01); *A61K 9/0019* (2013.01); *A61K 9/145* (2013.01); *A61K 9/2059* (2013.01); *A61K 9/4858* (2013.01); *A61K 31/4375* (2013.01); *C07C 229/24* (2013.01); *C07D 487/04* (2013.01)

(58) Field of Classification Search  
CPC .................................................... C07D 471/04  
USPC ....................................................... 546/123  
See application file for complete search history.

(56) References Cited

U.S. PATENT DOCUMENTS

| 6,753,430 | B2 | 6/2004 | Yoon et al. | |
|---|---|---|---|---|
| 7,767,860 | B2 * | 8/2010 | Gant et al. | .................... 564/506 |
| 8,664,240 | B2 | 3/2014 | Choi et al. | |
| 8,952,164 | B2 | 2/2015 | Choi et al. | |
| 2012/0130075 | A1 | 5/2012 | Choi et al. | |

FOREIGN PATENT DOCUMENTS

| KR | 10-0174373 | 2/1999 |
|---|---|---|
| KR | 10-2001-0029698 | 4/2001 |
| WO | WO 2008/127060 | 10/2008 |

OTHER PUBLICATIONS

Allen et al., "Multiple-Dose Pharmacokinetics and Tolerability of Gemifloxacin Administered Orally to Healthy Volunteers," Antimicrobial Agents and Chemotherapy (2001), 45(2), pp. 540-545.

Choi, et al, "Syntheses and biological evaluation of new fluoroquinolone antibacterials containing chiral oxiimino pyrrolidine," Bioorganic & Medicinal Chemistry Letters (2004), 14(5), 1273-1277.

Ekins, et al., "Insights for Human Ether-a-Go-Go-Related Gene Potassium Channel Inhibition Using Recursive Partitioning and Kohomen and Sammon Mapping Techniques," Journal of Medicinal Chemistry (2006), 49(17), 5059-5071.

Kim, et al., "Electrophysiological safety of DW-286a, a novel fluoroquinolone antibiotic agent," Human & Experimental Toxicology (2005), 24(1), 19-25.

PCT/KR2010/04938 International Search Report dated Apr. 27, 2011.

PCT/KR2010/04938 International Preliminary Report on Patentability Jan. 31, 2012.

PCT/KR2010/04938 Written Opinion dated Apr. 27, 2011.

U.S. Appl. No. 13/387,080 Notice of Allowance mailed Oct. 16, 2013.

U.S. Appl. No. 14/155,249 Non-Final Office action mailed Jun. 12, 2014.

U.S. Appl. No. 14/155,249 Notice of Allowance mailed Nov. 17, 2014.

* cited by examiner

*Primary Examiner* — Niloofar Rahmani  
(74) *Attorney, Agent, or Firm* — Wilson Sonsini Goodrich & Rosati

(57) ABSTRACT

Disclosed herein are R-7-(3-aminomethyl-4-methoxyimino-3-methyl-pyrrolidin-1-yl)-1-cyclopropyl-6-fluoro-4-oxo-1, 4-dihydro-[1,8]naphthyridine-3-carboxylic acid and L-aspartic acid salt, process for the preparation thereof and pharmaceutical composition comprising the same for antimicrobial. Because the R-7-(3-aminomethyl-4-methoxyimino-3-methyl-pyrrolidin-1-yl)-1-cyclopropyl-6-fluoro-4-oxo-1, 4-dihydro-[1,8]naphthyridine-3-carboxylic acid and L-aspartic acid salt is more soluble and less toxic and has less side effects as an antimicrobial agent than hydrochloride and the other salts (D-aspartate and phosphate) conventionally used, the salt may be useful for oral and injectable administration.

16 Claims, No Drawings

R-7-(3-AMINOMETHYL-4-METHOXYIMINO-3-METHYL-PYRROLIDIN-1-YL)-1-CYCLOPROPYL-6-FLUORO-4-OXO-1 ACID AND L-ASPARTIC ACID SALT, PROCESS FOR THE PREPARATION THEREOF AND PHARMACEUTICAL COMPOSITION COMPRISING THE SAME FOR ANTIMICROBIAL

CROSS REFERENCE

This application is a continuation of U.S. application Ser. No. 14/155,249 filed Jan. 14, 2014 which is a continuation patent application of U.S. application Ser. No. 13/387,080, filed Feb. 8, 2012 now issued as U.S. Pat. No. 8,664,240 pursuant to 35 U.S.C. §371 as a United States National Phase Application of, and which claims the right of priority to, International Application Ser. No. PCT/KR10/004938, filed Jul. 27, 2010, which claims the right of priority to Korean Application No. 10-2009-0068396, filed Jul. 27, 2009, all of which are incorporated by reference herein in their entirety.

TECHNICAL FIELD

The present disclosure relates to R-7-(3-aminomethyl-4-methoxyimino-3-methyl-pyrrolidin-1-yl)-1-cyclopropyl-6-fluoro-4-oxo-1,4-dihydro-[1,8]naphthyridine-3-carboxylic acid and L-aspartic acid salt, process for the preparation thereof and pharmaceutical composition comprising the same for antimicrobial.

BACKGROUND ART

Quinolone carboxylic acid derivatives are synthetic antibacterial agents which are well known to be useful for the treatment of infective diseases in human and animals due to their potent and broad antimicrobial activities. Currently, quinolone-based antimicrobial agents such as norfloxacin, ofloxacin, ciprofloxacin, etc. are very usefully applied for the treatment of human diseases, and their efficacies are acknowledged. However, these medicines have the problem that even though they show excellent antimicrobial activities against Gram-negative bacteria, they still show ordinary or relatively low antimicrobial activities against Gram-positive bacteria. Accordingly, there have been various studies for solving such problems of existing quinolone-based antimicrobial agents, and as a result, sparfloxacin having improved antimicrobial activities against Gram-positive bacteria has been developed. However, this compound still shows weak antimicrobial activities against *Streptococci*, methicillin resistant *Staphylococcus aureus* (MRSA) and other currently increasing quinolone-resistant strains. The above-mentioned strains are well known as pathogens of respiratory infections. Therefore, there are increasing needs for the development of improved quinolone antimicrobial agents which exhibit excellent antimicrobial activities against these strains.

In quinolone-based antimicrobial agents, R-7-(3-aminomethyl-4-methoxyimino-3-methyl-pyrrolidin-1-yl)-1-cyclopropyl-6-fluoro-4-oxo-1,4-dihydro-[1,8]naphthyridine-3-carboxylic acid exhibit excellent antimicrobial activities against Gram-positive bacteria, Gram-negative bacteria, methicillin resistant bacteria, and existing quinolone-resistant strains.

In general, it is well known to those skilled in the art that an active ingredient used in a pharmaceutical composition should be highly soluble in water or aqueous solution having a broad range of pH. Accordingly, the development of salts having excellent solubility is needed in order to increase the bioavailability of the R-7-(3-aminomethyl-4-methoxyimino-3-methyl-pyrrolidin-1-yl)-1-cyclopropyl-6-fluoro-4-oxo-1,4-dihydro-[1,8]naphthyridine-3-carboxylic acid.

Thus, the present inventors have described various salts of R-7-(3-aminomethyl-4-methoxyimino-3-methyl-pyrrolidin-1-yl)-1-cyclopropyl-6-fluoro-4-oxo-1,4-dihydro-[1,8]naphthyridine-3-carboxylic acid in Korean Patent Laid-Open Publication No. 2001-0029698. Examples of such acids are inorganic acids such as hydrochloric acid, phosphoric acid, sulfuric acid, etc., organic acids such as methanesulfonic acid, p-toluenesulfonic acid, acetic acid, citric acid, maleic acid, succinic acid, oxalic acid, benzoic acid, tartaric acid, fumaric acid, mandelic acid, lactic acid, glycolic acid, gluconic acid, galacturonic acid, glutamic acid, etc., and alkali metal ions such as sodium ions, potassium ions, etc. However, hydrochloride is usually used as a pharmaceutically acceptable salt of R-7-(3-aminomethyl-4-methoxyimino-3-methyl-pyrrolidin-1-yl)-1-cyclopropyl-6-fluoro-4-oxo-1,4-dihydro-[1,8]naphthyridine-3-carboxylic acid.

L-aspartic acid was approved by the US FDA as a food additive, and the acid has been safely and widely used. L-aspartic acid is a stable and colorless liquid that is not hygroscopic and corrosive and has stability in preparation because it is not toxic. It is so easy to treat the acid that L-aspartic acid may be easily used in mass production. In addition, the acid is known to contribute to hepatic detoxification, assist in mineral absorption, enhance DNA and RNA metabolism and improve immunocompetence. However, when L-aspartic acid is administered alone, the solubility and internal absorption is so low that only minor effects are known to be exerted when the acid is administered even in excess. Therefore, L-aspartic acid has not been conventionally used as a pharmaceutically acceptable salt.

Thus, the present inventors have performed research to develop a salt having excellent solubility to improve the bioavailability of the R-7-(3-aminomethyl-4-methoxyimino-3-methyl-pyrrolidin-1-yl)-1-cyclopropyl-6-fluoro-4-oxo-1,4-dihydro-[1,8]naphthyridine-3-carboxylic acid, prepared L-aspartate of R-7-(3-aminomethyl-4-methoxyimino-3-methyl-pyrrolidin-1-yl)-1-cyclopropyl-6-fluoro-4-oxo-1,4-dihydro-[1,8]naphthyridine-3-carboxylic acid, confirmed that the L-aspartate has better solubility as well as better physical properties such as stability, etc. than hydrochloride and D-aspartate, and aspartic acid is easily dissolved in the form of salt and internally absorbed to have a lower toxicity than the other salts, and made the present invention.

DISCLOSURE OF INVENTION

Technical Problem

One object of the present invention is to provide L-aspartate of R-7-(3-aminomethyl-4-methoxyimino-3-methyl-pyrrolidin-1-yl)-1-cyclopropyl-6-fluoro-4-oxo-1,4-dihydro-[1,8]naphthyridine-3-carboxylic acid.

Another object of the present invention is to provide a preparation method of the L-aspartate of R-7-(3-aminomethyl-4-methoxyimino-3-methyl-pyrrolidin-1-yl)-1-cyclopropyl-6-fluoro-4-oxo-1,4-dihydro-[1,8]naphthyridine-3-carboxylic acid.

Still another object of the present invention is to provide an antimicrobial pharmaceutical composition containing the L-aspartate of R-7-(3-aminomethyl-4-methoxyimino-3-methyl-pyrrolidin-1-yl)-1-cyclopropyl-6-fluoro-4-oxo-1,4-dihydro-[1,8]naphthyridine-3-carboxylic acid as an active ingredient.

Solution to Problem

In order to achieve the objects, the present invention provides L-aspartate of R-7-(3-aminomethyl-4-methoxyimino-3-methyl-pyrrolidin-1-yl)-1-cyclopropyl-6-fluoro-4-oxo-1, 4-dihydro-[1,8]naphthyridine-3-carboxylic acid, a preparation method thereof, and an antimicrobial pharmaceutical composition containing the same as an active ingredient.

Advantageous Effects of Invention

Because the R-7-(3-aminomethyl-4-methoxyimino-3-methyl-pyrrolidin-1-yl)-1-cyclopropyl-6-fluoro-4-oxo-1,4-dihydro-[1,8]naphthyridine-3-carboxylic acid L-aspartate of the present invention is more soluble than hydrochloride, is less toxic than the other salts (D-aspartate, hydrochloride, and phosphate), and has reduced side effects as an antimicrobial agent, the salt may be useful for oral and injectable administration.

BEST MODE FOR CARRYING OUT THE INVENTION

The present invention provides L-aspartate of R-7-(3-aminomethyl-4-methoxyimino-3-methyl-pyrrolidin-1-yl)-1-cyclopropyl-6-fluoro-4-oxo-1,4-dihydro-[1,8]naphthyridine-3-carboxylic acid represented by the following Chemical Figure 1.

Chemistry Figure 1

[Chem.1]

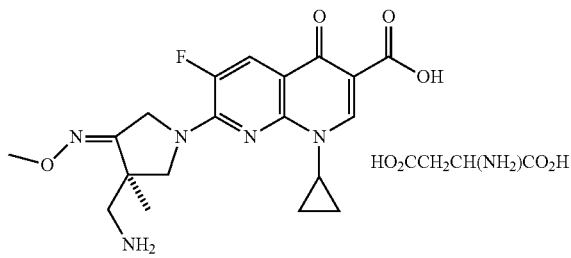

$HO_2CCH_2CH(NH_2)CO_2H$

R-7-(3-aminomethyl-4-methoxyimino-3-methyl-pyrrolidin-1-yl)-1-cyclopropyl-6-fluoro-4-oxo-1,4-dihydro-[1,8]naphthyridine-3-carboxylic acid L-aspartate of the present invention may be crystal or amorphous, and more preferably a crystal form.

The present invention also provides a preparation method of the R-7-(3-aminomethyl-4-methoxyimino-3-methyl-pyrrolidin-1-yl)-1-cyclopropyl-6-fluoro-4-oxo-1,4-dihydro-[1,8]naphthyridine-3-carboxylic acid L-aspartate of Chemical Figure 1. Specifically, a preparation method according to the present invention, as represented by the following Reaction Figure 1, includes reacting R-7-(3-aminomethyl-4-methoxyimino-3-methyl-pyrrolidin-1-yl)-1-cyclopropyl-6-fluoro-4-oxo-1,4-dihydro-[1,8]naphthyridine-3-carboxylic acid with L-aspartic acid in an inert organic solvent.

[Reaction FIG. 1]

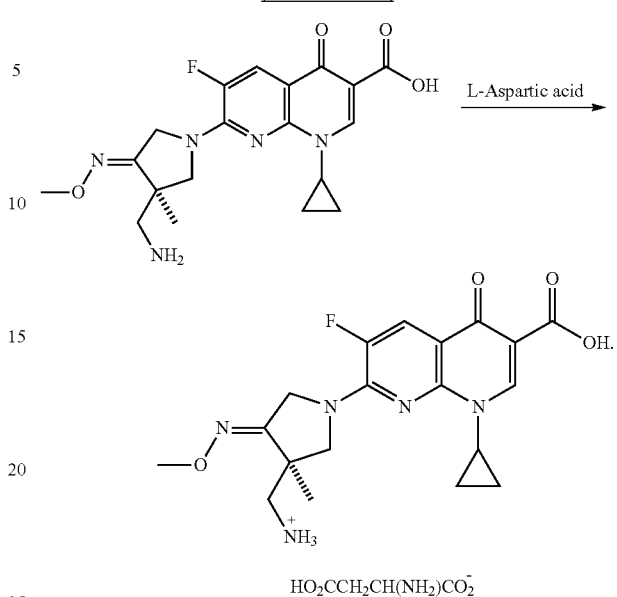

L-aspartic acid used in a preparation method according to the present invention has been widely used as a main ingredient of aspartame, is a stable and colorless liquid that is not hygroscopic and corrosive, and has stability in preparation because it is not toxic. It is so easy to treat the acid that L-aspartic acid may be easily used in mass production. In addition, because the acid is known to contribute to hepatic detoxification, assistance in mineral absorption, and enhancement of DNA and RNA metabolism and improve immunocompetence, it is expected that side effects accompanied by the use of antimicrobial agents may be reduced.

The inert organic solvent used in the preparation method of the present invention includes ethyl acetate, methanol, ethanol, isopropanol, acetone, acetonitrile, hexane, isopropyl ether, water, etc., and ethanol may be the most preferable among them.

A preparation method of the present invention will be specifically described as follows. First, R-7-(3-aminomethyl-4-methoxyimino-3-methyl-pyrrolidin-1-yl)-1-cyclopropyl-6-fluoro-4-oxo-1,4-dihydro-[1,8]naphthyridine-3-carboxylic acid is dissolved in an inert organic solvent. The inert organic solvent may be preferably used in an amount equivalent to a volume (ml) 10 to 20 times based on a weight (g) of R-7-(3-aminomethyl-4-methoxyimino-3-methyl-pyrrolidin-1-yl)-1-cyclopropyl-6-fluoro-4-oxo-1,4-dihydro-[1,8]naphthyridine-3-carboxylic acid.

0.9 to 2.5 equivalent weight, and preferably 1.0 to 1.5 equivalent weight of L-aspartic acid may be added to 1 equivalent weight of R-7-(3-aminomethyl-4-methoxyimino-3-methyl-pyrrolidin-1-yl)-1-cyclopropyl-6-fluoro-4-oxo-1, 4-dihydro-[1,8]naphthyridine-3-carboxylic acid and may be reacted at 30° C. to 70° C., and preferably 40° C. to 60° C. for 10 min to 5 hours, and preferably 30 min to 2 hours to prepare R-7-(3-aminomethyl-4-methoxyimino-3-methyl-pyrrolidin-1-yl)-1-cyclopropyl-6-fluoro-4-oxo-1,4-dihydro-[1,8]naphthyridine-3-carboxylic acid L-aspartate.

R-7-(3-aminomethyl-4-methoxyimino-3-methyl-pyrrolidin-1-yl)-1-cyclopropyl-6-fluoro-4-oxo-1,4-dihydro-[1,8]naphthyridine-3-carboxylic acid may be prepared at a high yield of 82-83% or more by the preparation method.

The present invention also provides an antimicrobial pharmaceutical composition containing R-7-(3-aminomethyl-4-methoxyimino-3-methyl-pyrrolidin-1-yl)-1-cyclopropyl-6-fluoro-4-oxo-1,4-dihydro-[1,8]naphthyridine-3-carboxylic acid L-aspartate of the Chemical Formula 1 as an active ingredient.

Furthermore, the present invention provides a method for treating bacterial disease, including administering to a patient in need thereof a therapeutically effective amount of L-aspartate of R-7-(3-aminomethyl-4-methoxyimino-3-methyl-pyrrolidin-1-yl)-1-cyclopropyl-6-fluoro-4-oxo-1,4-dihydro-[1, 8]naphthyridine-3-carboxylic acid represented by the Chemical Formula 1.

The present invention also provides a use of L-aspartate of R-7-(3-aminomethyl-4-methoxyimino-3-methyl-pyrrolidin-1-yl)-1-cyclopropyl-6-fluoro-4-oxo-1,4-dihydro-[1,8]naphthyridine-3-carboxylic acid represented by the Chemical Formula 1 in the preparation of an antimicrobial formulation.

L-aspartate of R-7-(3-aminomethyl-4-methoxyimino-3-methyl-pyrrolidin-1-yl)-1-cyclopropyl-6-fluoro-4-oxo-1,4-dihydro-[1,8]naphthyridine-3-carboxylic acid of the present invention was shown to have better solubility than R-7-(3-aminomethyl-4-methoxyimino-methyl-pyrrolidin-1-yl)-1-cyclopropyl-6-fluoro-4-oxo-1,4-dihydro-[1,8]naphthyridine-3-carboxylic acid, hydrochloride and D-aspartate thereof and to be about 2 times more soluble, in particular, in distilled water than the hydrochloride (See Table 1). There was also little change in content of the salt in distilled water, meaning that its chemical stability was excellent (See Table 2), and it was determined that the toxicity was relatively low due to a high lethal dose 50 (See Table 3). Furthermore, the salt exhibited pharmacokinetics equivalent to that of hydrochloride in an in vivo pharmacokinetic experiment (See Table 4).

Therefore, the L-aspartate according to the present invention may be useful as an antimicrobial agent.

A composition containing the L-aspartate according to the present invention may be used in the form of a general medicinal preparation.

That is, the L-aspartate according to the present invention may be administered in various dosage forms, orally or parenterally when administered in an actual clinical setting. Pharmaceutical preparations may be prepared by including one or more pharmaceutically acceptable carriers in addition to an active ingredient. The pharmaceutically acceptable carrier may be used by including saline solution, sterile water, Ringer's solution, buffered saline solution, dextrose solution, maltodextrin solution, glycerol, ethanol, and a mixture of one or more thereof, and other conventional additives such as antioxidants, buffers, bacteriostatic agents, etc. may be added if necessary.

Solid preparations for oral administration include tablets, pills, powders, granules, capsules, etc. These solid preparations may be prepared by mixing a compound with at least one excipients, for example, starch, calcium carbonate, sucrose, lactose, gelatin, etc. In addition to simple excipients, lubricants such as magnesium stearate and talc may be used.

In addition, liquid preparations for oral administration include suspensions, solutions, emulsions and syrups, etc. In addition to water commonly used as a simple diluent and liquid paraffin, various excipients, for example, wetting agents, sweetening agents, flavors, preservatives, etc. may be included. Preparations for parenteral administration include sterilized aqueous solutions, non-aqueous solvents, suspending agents, emulsions, freeze-drying agents, suppositories, etc. Propylene glycol, polyethylene glycol, vegetable oils such as olive oil, injectable esters such as ethyl oleate, etc. may be used as non-aqueous solutions and suspending agents. Suppositories may include witepsol, macrogol, tween 61, cacao butter, laurin butter, glycerinated gelatin, etc.

Furthermore, the pharmaceutical composition of the present invention may be parenterally administered, and the parenteral administration may be effected by hypodermatic, intravenous or intramuscular injection. To prepare a parenteral formulation, a solution or suspension may be prepared by mixing the compound with a stabilizer or a buffer in water, and a unit dosage form such as an ampoule or a vial may be prepared.

An amount of the L-aspartate according to the present invention may be preferably included in the ranges from 0.1% to 50% by weight based on a total weight of the composition. However, the above ranges are not to be limited to this, but may depend on the conditions of the patient, kinds of diseases, and severities of diseases.

A preferable dose of the L-aspartate according to the present invention depends on the conditions and body weight of the patient, the severity of the disease, drug forms, administration routes, and duration, but may be appropriately selected by those skilled in the art. However, 0.01 mg/kg to 10 g/kg a day, and preferably 1 mg/kg to 1 g/kg a day may be administered. The doses may be administered once or several times a day.

Mode for the Invention

Hereinafter, the present invention will be described in more detail with reference to the following examples and experimental examples. However, the following examples and experimental examples are provided for illustrative purposes only, and the scope of the present invention should not be limited thereto in any manner.

Example 1

Preparation of R-7-(3-aminomethyl-4-methoxyimino-3-methyl-pyrrolidin-1-yl)-1-cyclopropyl-6-fluoro-4-oxo-1,4-dihydro-[1,8]naphthyridine-3-carboxylic acid L-aspartate 23 ml of methanol and 23 ml of water were added to 7.8 g of R-7-(3-aminomethyl-4-methoxylimino-3-methyl-pyrrolidin-1-yl)-1-cyclopropyl-6-fluoro-4-oxo-1,4-dihydro-[1,8] naphthyridine-3-carboxylic acid, to which was added 2.57 g of L-aspartic acid, followed by stirring at 45° C. for 1 hour. After the solid of the reaction mixture was filtered, 78 ml of ethanol was added to the solid. The mixture was stirred at 5° C. to 10° C. for 2 hours, followed by filtration and drying to obtain 8.5 g of the target compound (yield: 82%).

$^1$H-NMR (D$_2$O, ppm): 1.03 (d, 2H, J=4.00 Hz), 1.27 (m, 2H), 1.47 (s, 3H), 2.67 (dd, 1H, J=17.59 Hz, J=8.80 Hz), 2.77 (dd, 1H, J=22.03 Hz, J=3.64 Hz), 3.34 (s, 2H), 3.63 (m, 1H), 3.86 (m, 1H), 3.96 (m, 5H), 4.67 (s, 2H), 7.66 (d, 1H, J=12.43 Hz), 8.54 (s, 1H).

Melting point (m.p.): 164.2° C.

Comparative Example 1

Preparation of R-7-(3-aminomethyl-4-methoxyimino-3-methyl-pyrrolidin-1-yl)-1-cyclopropyl-6-fluoro-4-oxo-1,4-dihydro-[1,8]naphthyridine-3-carboxylic acid D-aspartate 30 ml of methanol and 30 ml of distilled water were added to 10 g of R-7-(3-aminomethyl-4-methoxyimino-3-methylpyrrolidin-1-yl)-1-cyclopropyl-6-fluoro-4-oxo-1,4-dihydro-[1,8]naphthyridine-3-carboxylic acid, to which was added 3.3 g of D-aspartic acid, followed by stirring at 45° C. for 1 hour. After the solid of the reaction mixture was filtered, 100 ml of ethanol was added to the solid. The mixture was stirred at room temperature for 3 hours, and the solid produced was filtered and dried to obtain 8.67 g of the target compound (yield: 65%).

$^1$H-NMR (D$_2$O, ppm): 1.06 (2H, d, J=4.04 Hz), 1.32 (2H, d, J=6.96 Hz), 1.51 (3H, s), 2.73 (1H, dd, J=17.59 Hz, J=8.80 Hz), 2.83 (1H, dd, J=22.03 Hz, J=3.64 Hz), 3.38 (1H, s), 3.65 (2H, m), 3.90 (1H, m), 3.99 (4H, m), 4.10 (1H, m), 4.71 (2H, s), 7.68 (1H, d, J=12.27 Hz), 8.57 (1H, s).

Melting point (m.p.): 163.3° C.

Comparative Example 2

Preparation of R-7-(3-aminomethyl-4-methoxyimino-3-methyl-pyrrolidin-1-yl)-1-cyclopropyl-6-fluoro-4-oxo-1,4-dihydro-[1,8]naphthyridine-3-carboxylic acid According to the method described in Korean Patent Laid-Open Publication No. 2001-0029698, (+)-7-(3-aminomethyl-4-methoxyimino-3-methyl-pyrrolidin-1-yl)-1-cyclopropyl-6-fluoro-4-oxo-1,4-dihydro-[1,8]naphthyridine-3-carboxylic acid was prepared.

Comparative Example 3

Preparation of R-7-(3-aminomethyl-4-methoxyimino-3-methyl-pyrrolidin-1-yl)-1-cyclopropyl-6-fluoro-4-oxo-1,4-dihydro-[1,8]naphthyridine-3-carboxylic acid hydrochloride According to the method described in Korean Patent Laid-Open Publication No. 2001-0029698, (+)-7-(3-aminomethyl-4-methoxyimino-3-methyl-pyrrolidin-1-yl)-1-cyclopropyl-6-fluoro-4-oxo-1,4-dihydro-[1,8]naphthyridine-3-carboxylic acid hydrochloride was prepared.

Comparative Example 4

Preparation of R-7-(3-aminomethyl-4-methoxyimino-3-methyl-pyrrolidin-1-yl)-1-cyclopropyl-6-fluoro-4-oxo-1,4-dihydro-[1,8]naphthyridine-3-carboxylic acid methanesulfonate

*40 ml of trifluoroacetic acid was cooled to 5° C. to 10° C., to which was added 20 g of 7-[3-(t-butoxycarbonylamino-methyl)-4-methoxyimino-3-methyl-pyrrolidin-1-yl]-1-cyclopropyl-6-fluoro-4-oxo-1,4-dihydro-[1,8]naphthyridine-3-carboxylic acid, followed by stirring for 1.5 hours. 140 ml of isopropanol and 3.1 ml of methanesulfonic acid were added to this reaction mixture and stirred at the same temperature for 2 hours. The solid produced from the reaction mixture was filtered and dried to obtain 10.2 g of the target compound (yield: 51%).

$^1$H-NMR (D$_2$O, ppm): 1.05 (2H, d, J=3.84 Hz), 1.32 (2H, d, J=7.16 Hz), 1.51 (s, 3H), 2.80 (3H, s), 3.38 (2H, s), 3.67 (1H, in), 3.98 (4H, m), 4.10 (1H, m), 4.70 (2H, s), 7.65 (2H, d, J=12.27 Hz), 8.54 (1H, s).

Melting point (m.p.): 193.3° C.

Comparative Example 5

Preparation of R-7-(3-aminomethyl-4-methoxyimino-3-methyl-pyrrolidin-1-yl)-1-cyclopropyl-6-fluoro-4-oxo-1,4-dihydro-[1,8]naphthyridine-3-carboxylic acid formate 50 ml of purified water, 50 ml of ethanol, and 1.1 ml of formic acid were added to 10 g of R-7-(3-aminomethyl-4-methoxyimino-3-methyl-pyrrolidin-1-yl)-1-cyclopropyl-6-fluoro-4-oxo-1,4-dihydro-[1,8]naphthyridine-3-carboxylic acid, followed by stirring at 55° C. to 60° C. for 1 hour. Subsequently, the reaction mixture was filtered, and then 40 ml of ethanol was added to the filtrate. The mixture was cooled to room temperature and stirred at room temperature for 4 hours. The solid produced was filtered, followed by drying to obtain 6.4 g of the target compound (yield: 57%).

$^1$H-NMR (D$_2$O, ppm): 1.03 (2H, d, J=4.04 Hz), 1.31 (2H, in), 1.49 (3H, s), 3.37 (2H, s), 3.62 (1H, m), 3.95 (4H, m), 4.03 (1H, m), 4.66 (1H, s), 7.61 (2H, d, J=12.43 Hz), 8.45 (1H, s), 8.50 (1H, s).

Melting point (m.p.): 195.4° C.

Comparative Example 6

Preparation of R-7-(3-aminomethyl-4-methoxyimino-3-methyl-pyrrolidin-1-yl)-1-cyclopropyl-6-fluoro-4-oxo-1,4-dihydro-[1,8]naphthyridine-3-carboxylic acid phosphate 8.04 g of R-7-(3-aminomethyl-4-methoxyimino-3-methyl-pyrrolidin-1-yl)-1-cyclopropyl-6-fluoro-4-oxo-1,4-dihydro-[1,8]naphthyridine-3-carboxylic acid was added to 41 ml of phosphoric acid and 41 ml of distilled water, followed by stirring at 55° C. to 60° C. for 2 hours. Subsequently, the reaction mixture was filtered, and then the filtrate was cooled to room temperature. To the filtrate was added 33 ml of ethanol, and then the solid produced after the mixture was stirred at 5° C. to 10° C. for 1 hour was filtered and dried to obtain 8.54 g of the target compound (yield: 85%).

$^1$H-NMR (D$_2$O, ppm): 1.06 (2H, d, J=6.04 Hz), 1.32 (2H, d, J=6.96 Hz), 1.51 (3H, s), 3.38 (2H, s), 3.66 (1H, m), 3.99 (4H, s), 4.10 (1H, d, J=12.27 Hz), 4.70 (2H, s), 7.65 (111, d, J=12.23 Hz), 8.54 (1H, s).

Melting point (m.p.): 165.4° C.

Comparative Example 7

Preparation of R-7-(3-aminomethyl-4-methoxyimino-3-methyl-pyrrolidin-1-yl)-1-cyclopropyl-6-fluoro-4-oxo-1,4-dihydro-[1,8]naphthyridine-3-carboxylic acid p-toluenesulfonate 53 ml of ethanol and 53 ml of distilled water were added to 6 g of p-toluenesulfonic acid, to which was added 10.51 g of R-7-(3-aminomethyl-4-methoxyimino-3-methyl-pyrrolidin-1-yl)-1-cyclopropyl-6-fluoro-4-oxo-1,4-dihydro-[1,8]naphthyridine-3-carboxylic acid, followed by stirring at 55° C. to 58° C. for 2 hours. Subsequently, the reaction mixture was filtered, and then the filtrate was cooled to 5° C. to 10° C. 52 ml of ethanol was, added to the filtrate, followed by stirring for 1 hour. The solid produced was filtered and dried to obtain 8.24 g of the target compound (yield: 55%).

$^1$H-NMR (D$_2$O, ppm): 1.06 (2H, d, J=6.44 Hz), 1.31 (2H, d, J=6.96 Hz), 1.50 (3H, s), 2.35 (3H, s), 3.37 (2H, s), 3.66

(1H, m), 3.99 (4H, s), 4.11 (1H, d, J=12.1 Hz), 4.70 (2H, s), 7.31 (2H, d, J=8.44 Hz), 7.63 (2H, d, J=8.04 Hz), 7.68 (1H, d, J=12.2 Hz), 8.58 (1H, s).

Melting point (m.p.): 187.2° C.

Experimental Example 1

Solubility Test

Each solubility (µg/ml) of the R-7-(3-aminomethyl-4-methoxyimino-3-methyl-pyrrolidin-1-yl)-1-cyclopropyl-6-fluoro-4-oxo-1,4-dihydro-[1,8]naphthyridine-3-carboxylic acid L-aspartate, D-aspartate, methanesulfonate, formate, phosphate, p-toluenesulfonate, and hydrochloride and R-7-(3-aminomethyl-4-methoxyimino-3-methyl-pyrrolidin-1-yl)-1-cyclopropyl-6-fluoro-4-oxo-1,4-dihydro-[1,8]naphthyridine-3-carboxylic acid prepared in the Example and Comparative Examples was measured at room temperature.

The results are shown in Table 1.

TABLE 1

| Salt used | Solubility (mg/ml) |
| --- | --- |
| L-aspartate (Example 1) | 189.78 |
| D-aspartate (Comparative Example 1) | 118.64 |
| Free form (Comparative Example 2) | 2.79 |
| Hydrochloride (Comparative Example 3) | 93.30 |
| Methanesulfonate (Comparative Example 4) | 99.08 |
| Formate (Comparative Example 5) | 27.52 |
| Phosphate (Comparative Example 6) | 57.79 |
| p-toluenesulfonate (Comparative Example 7) | 5.78 |

As shown in Table 1, the free form of R-7-(aminomethyl-4-methoxyimino-3-methyl-pyrrolidin-1-yl)-1-cyclopropyl-6-fluoro-4-oxo-1,4-dihydro-[1,8]naphthyridine-3-carboxylic acid was rarely soluble in water due to the solubility of 2.79 mg/ml, while the L-aspartate according to the present invention was excellent in solubility, which was 189.78 mg/ml. In particular, the solubility of the L-aspartate according to the present invention was higher than that (118.64 mg/ml) of D-aspartate which is the optical isomer. The L-aspartate exhibited about 2 times higher solubility than the hydrochloride (93.30 mg/ml) and much better solubility than the other salts in Comparative Examples. Thus, the L-aspartate according to the present invention is excellent in solubility and may be useful as a medicine.

Experimental Example 2

Stability Test 30 mg of each salt of the R-7-(3-aminomethyl-4-methoxyimino-3-methyl-pyrrolidin-1-yl)-1-cyclopropyl-6-fluoro-4-oxo-1,4-dihydro-[1,8]naphthyridine-3-carboxylic acids prepared in the Example and Comparative Examples was dissolved in 100 ml of distilled water, and then was subjected to stability test at room temperature and at 60° C. The results are shown in Table 2.

TABLE 2

| | Content (%) | | |
| --- | --- | --- | --- |
| Salt used | Initial | Room temperature (after 3 weeks) | 60 ? (after 3 weeks) |
| L-aspartate (Example 1) | 98.1 | 98.0 | 87.4 |
| D-aspartate (Comparative Example 1) | 97.8 | 98.0 | 90.3 |
| Free form (Comparative Example 2) | 97.3 | 96.8 | 34.6 |
| Hydrochloride (Comparative Example 3) | 97.9 | 98.0 | 90.0 |
| Methanesulfonate (Comparative Example 4) | 96.4 | 96.8 | 89.6 |
| Formate (Comparative Example 5) | 89.7 | 89.7 | 75.1 |
| Phosphate (Comparative Example 6) | 98.1 | 97.9 | 91.2 |
| p-toluenesulfonate (Comparative Example 7) | 98.6 | 98.1 | 87.3 |

As shown in Table 2, there was little change in content of the L-aspartate according to the present invention at room temperature, meaning that it was chemically stable.

Experimental Example 3

Toxicity Test-Single Dose Toxicity in Mice

The following experiment was performed in order to observe the degree of toxicity of the L-aspartate according to the present invention.

Male ICR mice were used as experimental animals. 5 male ICR mice were divided into 6 dose groups, respectively and fasted except for water for 24 hours. R-7-(3-aminomethyl-4-methoxyimino-3-methyl-pyrrolidin-1-yl)-1-cyclopropyl-6-fluoro-4-oxo-1,4-dihydro-[1,8]naphthyridine-3-carboxylic acid L-aspartate prepared in the Example 1 and the other salts prepared in Comparative Examples were intraperitoneally administered once (10 ml/kg) at 500, 250, 125, and 0 mg/kg, respectively to observe the lethal dose 50 (LD50) for 14 days. The results are shown in Table 3.

TABLE 3

| Salt used | Lethal dose 50 (mg/kg) |
| --- | --- |
| L-aspartate (Example 1) | 209 |
| D-aspartate (Comparative Example 1) | 176 |
| Hydrochloride (Comparative Example 3) | 176 |
| Phosphate (Comparative Example 6) | 176 |

As shown in Table 3, it is determined that the L-aspartate of the present invention was less toxic than the other salts (D-aspartate, phosphate, and hydrochloride) due to a higher lethal dose 50 than those of the other salts.

Experimental Example 4

In Vivo Genotoxicities

The following study performed to obtain in vivo genotoxicities, micronucleus test of L-aspartate and hydrochloric acid salt in male mice to the following procedure.

After 24 hrs after end of twice intraperitoneal treatment of aspartate or of single intraperitoneal treatment of cyclophosphamide (CPA), all animal were sacrifice and the changes on the number of polychromatic erythrocyte with one or more nuclei (MNPCE) were evaluate among 2000 PCEs with PCE/((PCE+normochromatic erythrocytes (NCE)) ratio among 500 erythrocytes for detecting possibility of cytotoxicity. The highest dosage used in the present study was selected as 60 mg/kg in a volume of 20 ml using distilled water as vehicle because quinolone antibiotics have been showed positive results in mouse micronucleus test, and 30, 15 and 7.5 mg/kg were selected using common ratio 2 in the present study, respectively. In addition, intact control and positive control (cyclophosphoamide (CPA) 70 mg/kg) groups were added.

In these result, the MNPCE number of aspartate were not detected significant change in 30, 15, 7.5 ing/kg treat group as compared with intact control, respectively. But in the case of hydrochloric acid salt, the MNPCE number were significantly increase in 7.5 mg/kg tested group.

Experimental Example 5

In Vivo Pharmacokinetic Test

The L-aspartate and hydrochloride according to the present invention were orally or intravenously administered to SD rats, respectively and blood samples were collected at a predetermined time to compare in vivo pharmacokinetics. Pharmacokinetic parameters are shown in Table 4.

Then, Cmax: maximum drug concentration, Tmax: maximum drug concentration time, $T_{1/2}$: drug half-life, AUC0-t: area under the plasma concentration-time curve from time zero to t hours, and AUC0-inf: area under the plasma concentration-time curve from time zero to infinity.

TABLE 4

PK parameters of the hydrochloride and L-aspartate according to the present invention in rats after p.o. and i.v. administration

| Pharmaco kinetic parameter | Hydrochloride | | L-aspartate | |
|---|---|---|---|---|
| | i.v. (10 mg/kg) | p.o. (100 mg/kg) | i.v. (10 mg/kg) | p.o. (100 mg/kg) |
| $C_{max}$ (µg/ml) | 4.46 ± 0.96 | 7.62 ± 3.93 | 4.18 ± 0.29 | 9.08 ± 4.50 |
| $T_{max}$ (hr) | 0 | 2.13 ± 1.97 | 0 | 2.13 ± 0.63 |
| $T_{1/2}$ (hr) | 1.552.05± | — | 2.05 ± 1.55 | — |
| $AUC_{0-t}$ (µg · hr/ml) | 8.72 ± 0.33 | 44.42 ± 21.38 | 7.52 ± 0.22 | 52.68 ± 28.73 |
| $AUC_{0-inf}$ (µg · hr/ml) | 0.4610.72± | — | 9.32 ± 0.28 | — |
| BA(%)a | — | 50.96 | — | 70.05 |

* estimated value by back extrapolation($C_0$)
aThis result is calculated by ratio of $AUC_{0-T}$ The pharmacokinetic parameters of the hydrochloride and L-aspartate according to the present invention showed in Table 4. Although the statistical significance was not observed, the mean oral bioavailability (BA, %) of the L-aspartate of the present invention was relatively higher than that of the hydrochloride in rat pharmacokinetic study. The BA values of the hydrochloride and L-aspartate according to the present invention were 50.96% and 70.05%, respectively.

Experimental Example 6

In Vivo Tissue Distribution Test

An in vivo tissue distribution test was performed in order to confirm the degree of drug distribution of the L-aspartate and hydrochloride according to the present invention in each organ. After 8-week-old ICR mice were purchased and adapted in the laboratory, each salt was orally administered to the mouse at a dose of 100 mg/kg. The mice were bled and sacrificed at a predetermined time and each organ was drawn to measure the concentration in each organ. After the administration of hydrochloride and L-aspartate, each organ concentration over time, the area under the corresponding time-concentration curve, and the ratio of permeation into tissue were shown in Tables 5 and 6.

Then, P ratio is a ratio of permeation into muscle and calculated as intramuscular AUC/intraplasmic AUC.

TABLE 5

| | Hydrochloride | | | | | | | | | |
|---|---|---|---|---|---|---|---|---|---|---|
| Time (hr) | Plasma (µg/ml) | Liver (µg/g) | Kidney (µg/g) | Brain (µg/g) | Lung (µg/g) | Spleen (µg/g) | Thymus (µg/g) | Heart (µg/g) | Testicle (µg/g) | Muscle (µg/g) |
| 0.5 | 15.51 | 160.68 | 90.76 | 2.51 | 82.80 | 101.81 | 24.55 | 59.29 | 4.79 | 39.79 |
| 1 | 14.24 | 124.93 | 87.84 | 3.09 | 79.50 | 111.78 | 57.95 | 61.22 | 8.36 | 52.03 |

TABLE 5-continued

Hydrochloride

| Time (hr) | Plasma (µg/ml) | Liver (µg/g) | Kidney (µg/g) | Brain (µg/g) | Lung (µg/g) | Spleen (µg/g) | Thymus (µg/g) | Heart (µg/g) | Testicle (µg/g) | Muscle (µg/g) |
|---|---|---|---|---|---|---|---|---|---|---|
| 1.5 | 12.09 | 112.52 | 75.49 | 2.72 | 73.65 | 107.26 | 60.77 | 52.66 | 12.66 | 50.40 |
| 2 | 12.04 | 109.11 | 69.92 | 3.18 | 63.66 | 101.77 | 61.30 | 57.59 | 16.98 | 50.82 |
| 3 | 6.24 | 68.98 | 42.99 | 1.99 | 38.75 | 59.75 | 38.37 | 25.52 | 14.22 | 28.30 |
| 5 | 4.32 | 55.73 | 32.76 | 1.60 | 23.42 | 42.08 | 25.68 | 17.31 | 12.92 | 18.42 |
| 8 | 2.29 | 27.03 | 18.04 | 0.73 | 11.41 | 21.51 | 12.82 | 8.86 | 7.77 | 8.26 |
| $AUC_{0-t}$ | 53.55 | 564.25 | 352.92 | 14.63 | 299.50 | 463.83 | 258.57 | 224.61 | 90.91 | 210.10 |
| P ratio | — | 10.54 | 6.59 | 0.27 | 5.59 | 8.66 | 4.83 | 4.19 | 1.70 | 3.92 |

TABLE 6

L-aspartate

| Time (hr) | Plasma (µg/ml) | Liver (µg/g) | Kidney (µg/g) | Brain (µg/g) | Lung (µg/g) | Spleen (µg/g) | Thymus (µg/g) | Heart (µg/g) | Testicle (µg/g) | Muscle (µg/g) |
|---|---|---|---|---|---|---|---|---|---|---|
| 0.5 | 11.59 | 127.50 | 79.15 | 2.28 | 76.28 | 91.63 | 26.52 | 47.22 | 4.94 | 38.02 |
| 1 | 12.24 | 114.15 | 79.20 | 2.55 | 70.10 | 98.14 | 48.11 | 57.97 | 8.82 | 39.58 |
| 1.5 | 10.74 | 117.77 | 77.42 | 2.34 | 71.52 | 84.89 | 48.85 | 49.96 | 10.20 | 37.37 |
| 2 | 8.47 | 85.44 | 62.18 | 2.57 | 52.69 | 67.28 | 40.10 | 36.69 | 12.92 | 36.70 |
| 3 | 6.30 | 70.82 | 48.76 | 2.02 | 38.74 | 57.56 | 39.78 | 27.72 | 14.84 | 28.83 |
| 5 | 4.62 | 57.35 | 34.03 | 1.52 | 24.52 | 43.72 | 25.94 | 01.33 | 11.52 | 18.02 |
| 8 | 1.87 | 26.56 | 20.17 | 0.33 | 11.62 | 23.37 | 12.79 | 8.72 | 6.97 | 6.93 |
| $AUC_{0-t}$ | 47.44 | 533.23 | 353.00 | 12.82 | 285.27 | 418.47 | 235.49 | 203.05 | 83.15 | 183.68 |
| P ratio | — | 11.24 | 7.44 | 0.27 | 6.01 | 8.82 | 4.96 | 4.28 | 1.75 | 3.87 |

As shown in Tables 5 and 6, when the L-aspartate and hydrochloride according to the present invention was orally administered, there was no big difference in concentration of the drug to be distributed in organ tissues and AUC according to the form of salt. It was confirmed that the levels of the L-aspartate according to the present invention permeated were highest in the order of liver, kidney, brain, spleen, lung, thymus, heart, muscle, and testicle.

Preparation Example

Preparation of Pharmaceutical Formulations

<1-1> Preparation of Powders
Compound of Chemical Formula 1 2 g
Lactose 1 g
The ingredients were mixed and filled into sealed packaging to provide powders.

<1-2> Preparation of a Tablet
Compound of Chemical Formula 1 100
Corn starch 100
Lactose 100
Magnesium stearate 2
The ingredients were mixed and tableted according to a conventional tablet preparation method to provide a tablet.

<1-3> Preparation of a Capsule
Compound of Chemical Formula 1 100
Corn starch 100
Lactose 100
Magnesium stearate 2
The ingredients were mixed and filled into a gelatin capsule according to a conventional capsule preparation method to provide a capsule.

<1-4> Preparation of Injections
Compound of Chemical Formula 1 10/
Diluted Hydrochloric acid BP to pH 3.5
Injectable Sodium chloride BP Up to 1
The compound of Chemical Formula 1 was dissolved in a proper volume of injectable sodium chloride BP, pH of a solution produced was adjusted to pH 3.5 with diluted hydrochloric acid BP, and its volume was adjusted with injectable sodium chloride BP. After being sufficiently mixed, the solution was filled in a 5 type I ampoule made from transparent glass, which was then molten such that the solution was packaged under the upper grid of air. An injection was obtained by autoclaving the ampoule at 120° C. for 15 min or longer.

The invention claimed is:

1. A method for preparing L-aspartate of a quinolone antimicrobial agent, comprising reacting the quinolone antimicrobial agent with L-aspartic acid in an inert organic solvent that comprises ethyl acetate, methanol, ethanol, isopropanol, acetone, acetonitrile, hexane, isopropyl ether, or water, wherein the quinolone antimicrobial agent comprises norfloxacin, ofloxacin, ciprofloxacin, sparfloxacin, or combinations thereof, provided that about 0.9 to about 2.5 equivalent weight of the L-aspartic acid is added to about 1 equivalent weight of the quinolone antimicrobial agent.

2. The method of claim 1, provided that the quinolone antimicrobial agent is active against Gram-positive bacteria, Gram-negative bacteria, or methicillin resistant bacteria.

3. A method of improving water solubility of a quinolone antimicrobial agent, comprising converting the quinolone antimicrobial agent into a pharmaceutically acceptable L-aspartate salt in an inert organic solvent that comprises ethyl acetate, methanol, ethanol, isopropanol, acetone, acetonitrile, hexane, isopropyl ether, or water, wherein the quinolone antimicrobial agent comprises norfloxacin, ofloxacin, ciprofloxacin, sparfloxacin, or combinations thereof, provided that about 0.9 to about 2.5 equivalent weight of L-aspartic acid is added to about 1 equivalent weight of the quinolone antimicrobial agent.

4. The method of claim 3, provided that the salt has water solubility of at least about 100 mg/ml at room temperature.

5. The pharmaceutically acceptable salt of claim 3, provided that the salt has water solubility of at least about 118 mg/ml at room temperature.

6. The method of claim 3, provided that the salt has a greater mean oral bioavailability than a hydrochloric acid salt of the quinolone antimicrobial agent.

7. The method of claim 6, provided that the salt has at least about a 30% greater mean oral bioavailability than a hydrochloric acid of the quinolone antimicrobial agent.

8. The method of claim 3, provided that the quinolone antimicrobial agent is active against Gram-positive bacteria, Gram-negative bacteria, or methicillin resistant bacteria.

9. The method of claim 1, provided that the quinolone antimicrobial agent comprises norfloxacin.

10. The method of claim 1, provided that the quinolone antimicrobial agent comprises ofloxacin.

11. The method of claim 1, provided that the quinolone antimicrobial agent comprises ciprofloxacin.

12. The method of claim 1, provided that the quinolone antimicrobial agent comprises sparfloxacin.

13. The method of claim 3, provided that the quinolone antimicrobial agent comprises norfloxacin.

14. The method of claim 4, provided that the quinolone antimicrobial agent comprises ofloxacin.

15. The method of claim 5, provided that the quinolone antimicrobial agent comprises ciprofloxacin.

16. The method of claim 6, provided that the quinolone antimicrobial agent comprises sparfloxacin.

* * * * *